United States Patent [19]
Docter

[11] Patent Number: 6,143,946
[45] Date of Patent: Nov. 7, 2000

[54] THERAPEUTIC MAT

[76] Inventor: Joan E. Docter, 733-D Residenz Pkwy., Dayton, Ohio 45429

[21] Appl. No.: 09/220,819

[22] Filed: Dec. 24, 1998

[51] Int. Cl.[7] ....................................................... A61F 13/00
[52] U.S. Cl. ................................. 602/41; 602/42; 602/43; 602/44; 602/45; 602/46; 602/47; 602/48; 602/49; 602/50; 602/51; 602/52; 602/53; 602/54; 602/55; 602/56; 602/57; 602/58; 602/59
[58] Field of Search .................................. 602/41, 42, 43, 602/44, 45, 46, 47, 48, 49, 50, 51–59

[56] References Cited

U.S. PATENT DOCUMENTS 5,538,500  7/1996  Peterson .
5,660,854  8/1997  Haynes et al. .
5,843,025  12/1998  Shaari .
5,977,428  11/1999  Bozigian et al. .

FOREIGN PATENT DOCUMENTS

0606512A1  1/1993  European Pat. Off. .

*Primary Examiner*—Michael A. Brown
*Assistant Examiner*—Lalita Hamilton
*Attorney, Agent, or Firm*—R. William Graham

[57] ABSTRACT

A therapeutic mat for application to a person includes a relatively elastic substrate of a predetermined size, a hydrogel substance connected to the elastic substrate, and a plurality of microcrystals dispersed throughout the hydrogel substance. The therapeutic mat may further include retaining straps connectable to the elastic substrate and of a size and configuration to extend about the part of the body for supporting the therapeutic mat in a relatively fixed position.

8 Claims, 1 Drawing Sheet

THERAPEUTIC MAT

BACKGROUND OF THE INVENTION

1. Field of the Invention

The present invention relates to the field of crystal therapies for holistic treatment of bodily wounds, injuries, aging skin disorders and diseases. More particularly, the present invention is directed to a therapeutic mat which incorporates crystals for treating the body.

2. Related Art

There is a growing awareness of the effects of crystals and their purported ability to aid in the healing process of an individual. It is thought that the crystals enable what is called "vibrational medicine." This belief is predicated upon the fact that crystals, such as quartz, vibrate at particular frequencies which play a role in placing a dysfunctional body back in harmonious synchronization. To expand, our bodies vibrate at certain frequencies, as our body is comprised of molecules, the greater part of which is water, and these molecules continuously vibrate at certain frequencies. Under a healthy state of condition, these molecules vibrate at a certain frequency, whereas when we are unhealthy, these molecules vibrate at another frequency.

Crystals are thought to aid in returning and/or keeping these molecules at vibrational frequencies which promote healthy conditions. There exist several techniques for using such crystals. One known technique for treating and/or promoting healing employs the use of crystals in settings which are hung on the body. Another employs crystals in an emollient cream which aids in retaining the crystals to the skin. Other approaches have included the use of blends of various types of crystals for the treatment of certain functions of the body.

A problem which exists with such treatment resides in the application process of crystal therapies. The application of crystals on the body is awkward. Wearing large bulky nugget-type crystals is not desirable, although easier to affix to a handing device, like a chain. Smaller crystals are desirable, but heretofore have only been employed in an emollient cream base which is rubbed onto the skin. The emollient cream base is not appealing because it tends to clog pores of the body, is not easily washed off, and depending upon the composition may stain clothing and therefore is not really suitable for continuous wearing.

There is a need for a suitable application of crystal therapy which is capable of keeping the crystals in a proper nexus to the skin of the body, while not having undesirable effects associated with direct application of the crystals to the skin. Further, there is a need to have such crystals be self-sustaining in a position which is substantially non-traumatic to the injury or treatment site.

BRIEF SUMMARY OF THE INVENTION

It is an object to improve healing treatment using crystal therapy.

It is a further object to improve application of crystals in treatment.

The present invention is directed to a therapeutic mat for application to skin of a patient. The therapeutic mat includes a relatively elastic substrate having a predetermined size, a hydrogel substance connected to the elastic substrate, and a plurality of microcrystals dispersed throughout the hydrogel substance. The therapeutic mat may further include retaining straps connectable to the elastic substrate and of a size and configuration to extend about the part of the body for supporting the therapeutic mat in a relatively fixed position.

Other objects and advantages will be readily apparent to those skilled in the art upon viewing the drawings and reading the detailed description hereafter.

DETAILED DESCRIPTION OF THE INVENTION

Figure 1:
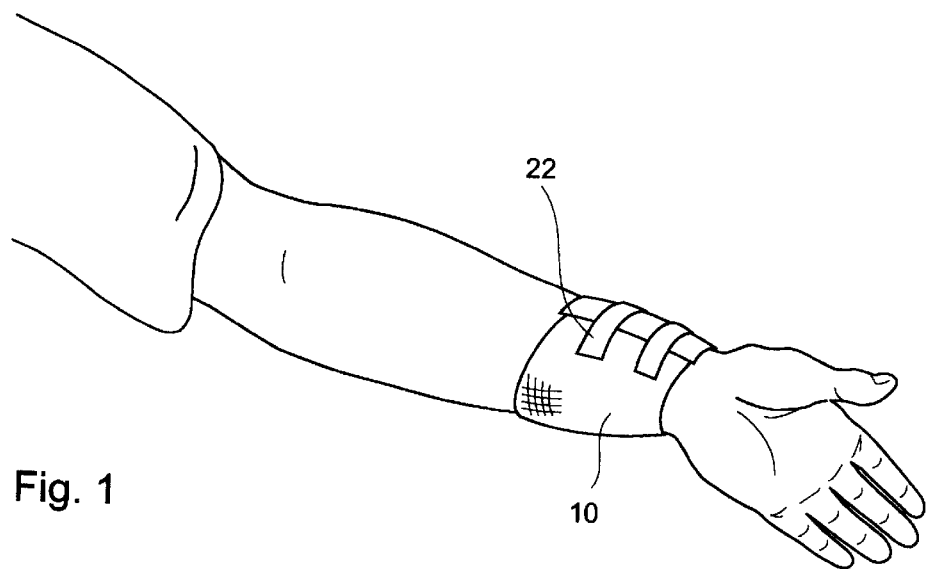
FIG. 1 is a perspective view of the present invention in use on a person.
Figure 2:
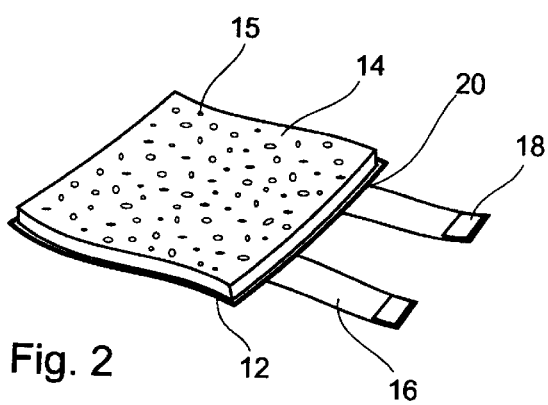
FIG. 2 is a perspective view of the present invention.
Figure 3:
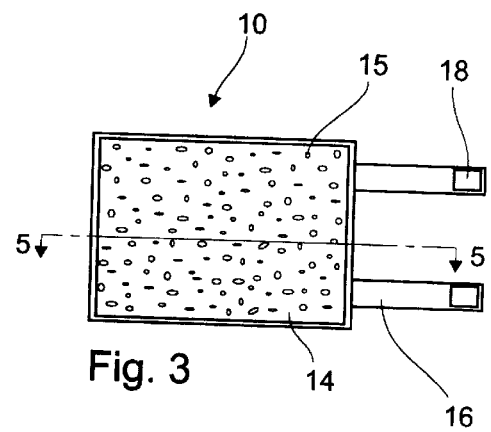
FIG. 3 is a front view of the present invention.
Figure 5:
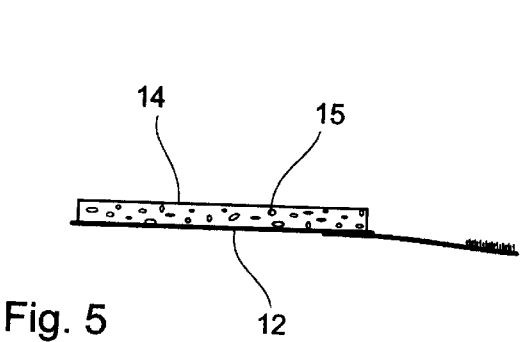
FIG. 5 is a cross-sectional view of the present invention taken through line 5—5 of FIG. 3.
Figure 4:
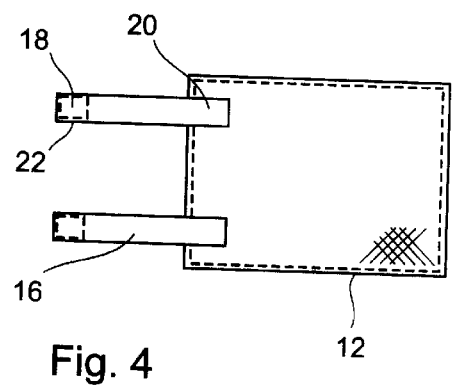
FIG. 4 is a back view of the present invention.

Referring now to the drawings, a therapeutic mat of the present invention is generally referred to by the numeral 10. The therapeutic mat 10 is designed for application to a body part, such as a wrist of a person P (or animal) who suffers from arthritis. The therapeutic mat may also be employed in treating wounds as a result of ulceration, burns, abrasions, angina, carpal tunnel, broken bones, fractures, wounds and incisions, for example.

The therapeutic mat 10 includes a slightly elastic substrate 12, a hydrogel material 14, crystals 15 and retaining straps 16. The hydrophilic gel 14 is connectedly applied to the substrate 12 so that the gel 14 sticks to the substrate 12. The crystals 15 are dispersed throughout the hydrogel material 14.

The substrate 12 is preferably made of a fabric material, such as a spandex material, and is tubular to permit sliding the same over the head of the patient P. The substrate 12 should have sufficient elasticity to accommodate expansion which occurs during the absorption of the fluids in the hydrogel 14. Additionally, the substrate 12 should also be of sufficient strength and inelasticity to maintain the gel 14 in a relatively fixed position with respect to the substrate 12 as fluid is adsorbed. The length and width of the mat 10 should be sufficient to cover the treated area.

The hydrogel 14 of the present invention is preferably one which has bacteriostatic properties and is highly absorptive. The hydrogel 14 may include substances such as hydropropyl methyl cellulose, ethylene glycol, propylene glycol, dimethyl oxide, dimethyl formamide, poly-2-hydroxyethelymethacrylate, or hydrocolloid with pectin or carboxymethyl cellulose, for example, the selection of which is partially predicated upon the degree of absorptivity required. The other property of the hydrogel is that it suitable to retain the crystals in a dispersed fashion therein and be of a composition which allows for vibrational propagational frequencies of the crystals 15 to be maximized.

In addition, the hydrogel material 14 may include a therapeutically effective amount of vitamin. Such vitamins may include vitamin A, B, C, D, E, for example. Other mineral additives, such as zinc, iron, copper, selenium, calcium, for example, may also be added to the mat 10 of the present invention. The amount and selection of vitamin or mineral to be added should not be substantially deleterious to the operation of the hydrogel or crystal vibrational treatment of the present invention.

The crystals 15 of the present invention are ground into a fine powder like thereby rendering them "microcrystals" and may include quartz, ruby, emerald, citrine, turquoise, amethyst, limestone, opal, zircon, agate, aventurine, tourmaline, amber, jade, sapphire, diamond and manganese, the selections of which is predicated upon the disease and area of the body to be treated. It is also desirable that the crystals be ground to a relatively fine powder in order to increase the surface area of the crystals and their structure. It is believed that increasing the surface area further enhances the vibrational therapy and aids in dispersability of the crystals within the hydrogel material 14.

The retaining straps 16 are connected to the elastic substrate 12 via Velcro™ hook and loop fasteners 18 obtainable from the Velcro Corporation wherein an end 20 is connected to the substrate 12 in a fixed manner and another end 22 of the retaining straps 16 wrap about the body part of the person P to fasten to the substrate 12 to secure the therapeutic mat 10 in place. The retaining straps 16 are of a size and configuration to extend about the head of the patient for supporting the therapeutic mat in a relatively fixed position on the patient's face and have sufficiently sized Velcro™ fasteners to accommodate varying sized heads. While the retaining straps 16 are shown as connected to the substrate 12 in a particular embodiment, it will be readily apparent to one skilled in the art that other retaining configurations can be employed to carry out this aspect of the invention.

The above described embodiment is set forth by way of example and is not for the purpose of limiting the present invention. It will be readily apparent to those skilled in the art that obvious modifications, derivations and variations can be made to the embodiment without departing from the scope of the invention. Accordingly, the claims appended hereto should be read in their full scope including any such modifications, derivations and variations.

What is claimed is:

1. A therapeutic mat for application to a person and an animal, which includes:
    a substrate;
    a hydrogel substance connectedly applied to said substrate; and
    a plurality of micro crystal in powder form dispersed throughout said hydrogel substance, wherein said substrate exhibits sufficient elasticity to accommodate expansion which occurs during absorption of fluid by said hydrogel substance, and sufficient strength and inelasticity to maintain said gel substance in a relatively fixed position with respect to said substrate as the fluid is absorbed.

2. The therapeutic mat of claim 1, which further includes at least one retaining strap of a size and configuration to extend about a body part of person for supporting said therapeutic mat in a relatively fixed position on the body part.

3. The therapeutic mat of claim 2, wherein said retaining strap is removably connectable to said elastic substrate.

4. The therapeutic mat of claim 2, wherein the crystals are selected from the group consisting of quartz, ruby, emerald, citrine, turquoise, amethyst, limestone, opal, zircon, agate, aventurine, tourmaline, amber, jade, sapphire, diamond and manganese.

5. The therapeutic mat of claim 1, wherein said hydrogel is characterized to be absorptive and having bacteriostatic and analgesic properties with sufficient stability to retain said microcrystals therein.

6. The therapeutic mat of claim 1, wherein said hydrogel includes vitamins selected from the group consisting of vitamin A, B, C, D, and E.

7. The therapeutic mat of claim 1, wherein said hydrogel includes minerals selected from the group consisting of zinc, iron, copper, selenium, and calcium.

8. A therapeutic mat for application to a person and and animal, which includes:
    a substrate;
    a hydrogel substance connectedly applied to said substrate; and
    a plurality of micro crystals selected from the group consisting of quartz, ruby, emerald, citrine, turquoise, amethyst, limestone, opal, zircon, agate, aventurine, tourmaline, amber, jade, sapphire, diamond, manganese, and mixtures thereof in powder form dispersed throughout said hydrogel substance, wherein said substrate exhibits sufficient elasticity to accommodate expansion which occurs during absorption of fluid by said hydrogel substance, and sufficient strength and inelasticity to maintain said gel is a relatively fixed position with respect to said substances fluid is absorbed.

* * * * *